(12) United States Patent
Lebel et al.

(10) Patent No.: US 9,398,981 B2
(45) Date of Patent: Jul. 26, 2016

(54) REVERSIBLE STRAP-MOUNTING CLIPS FOR GOGGLES (75) Inventors: Stéphane Lebel, St.-Rédempteur (CA); Dominique Croteau, Montreal (CA)

(73) Assignee: Revision Military Inc., Montreal (CA)

( * ) Notice: Subject to any disclaimer, the term of this patent is extended or adjusted under 35 U.S.C. 154(b) by 0 days.

(21) Appl. No.: 13/482,700

(22) Filed: May 29, 2012

(65) Prior Publication Data

US 2012/0233734 A1    Sep. 20, 2012

Related U.S. Application Data (63) Continuation of application No. 12/210,981, filed on Sep. 15, 2008, now abandoned.

(60) Provisional application No. 60/993,677, filed on Sep. 13, 2007.

(51) Int. Cl.
A61F 9/02    (2006.01)

(52) U.S. Cl.
CPC .................. *A61F 9/027* (2013.01); *A61F 9/029* (2013.01)

(58) Field of Classification Search
CPC ....................................................... A61F 9/027
USPC .......................... 2/426, 448, 452; 351/156, 43
See application file for complete search history.

(56) References Cited

U.S. PATENT DOCUMENTS

| 4,150,443 A | 4/1979 | McNeilly |
|---|---|---|
| 4,868,929 A | 9/1989 | Curcio |
| 4,942,629 A | 7/1990 | Stadlmann |
| 4,968,127 A | 11/1990 | Russell et al. |
| 5,172,256 A | 12/1992 | Sethofer et al. |
| 5,379,140 A | 1/1995 | Michel et al. |
| 5,666,663 A * | 9/1997 | Bolle ................................. 2/10 |
| 6,732,383 B2 | 5/2004 | Cleary et al. |
| 6,928,663 B1 | 8/2005 | Tappeiner |
| 7,003,811 B2 * | 2/2006 | Canavan ........................ 2/448 |
| 7,567,306 B2 | 7/2009 | Park et al. |
| 2003/0037367 A1 | 2/2003 | Fukasawa |
| 2005/0193478 A1 | 9/2005 | Hussey |
| 2009/0307828 A1 | 12/2009 | Ludlow |

FOREIGN PATENT DOCUMENTS

CN    1475198 A    2/2004

OTHER PUBLICATIONS

International Search Report and Written Opinion for PCT/US08/76460, mailed Jun. 26, 2015.

* cited by examiner

*Primary Examiner* — Katherine Moran
(74) *Attorney, Agent, or Firm* — Wolf, Greenfield & Sacks, P.C.

(57) ABSTRACT

Goggles include a strap, a frame, at least one lens, and first and second connectors. The strap has opposite strap free ends. The frame has a lateral center and opposite lateral end portions. Each connector has a base portion for connecting to the opposite lateral end portion of the frame, and a strap-mounting portion for connecting to the opposite strap free end of the strap. Each strap-mounting portion has a strap connecting end where the strap meets the strap-mounting portion. Each of the first and second connectors have a first orientation for helmet-less usage and a second orientation for helmet usage. The strap connecting end of each connector is located a greater distance from the lateral center of the frame when the connector is in a second orientation than when in the first orientation.

8 Claims, 12 Drawing Sheets

FIG 13

REVERSIBLE STRAP-MOUNTING CLIPS FOR GOGGLES

This application is a continuation of U.S. application Ser. No. 12/210,981 filed Sep. 15, 2008, now abandoned, which claims the benefit of U.S. Provisional Application Ser. No. 60/993,677, filed Sep. 13, 2007.

TECHNICAL FIELD OF THE INVENTION

The present invention relates to strap attaching arrangements provided on goggles.

BACKGROUND OF THE INVENTION

Specially adapted, protective goggles are used today by soldiers and law enforcement officers. The use of such protective goggles is particularly advantageous in harsh environments where sunlight, wind, dust and debris can be hazardous to eyesight. Additionally, such protective goggles can be designed to protect the eyes against some level of impact of fragments and projectiles during combat or law enforcement activities. Such eyewear includes Bullet Ant™ goggles or Desert Locust™ goggles available from Revision Military of Montreal, Canada, or Revision Eyewear, Ltd. of Essex Jct., Vt., USA. These goggles are often configured to be strapped over a protective helmet.

Protective goggles are also used in industrial applications, or in sports, such as skiing or snowboarding, worn with or without a helmet.

Goggles are traditionally retained on the user's head by use of a strap with opposite ends that attach to clip portions located on opposite lateral ends of the goggle frame wherein the strap passes behind the user's head. A strap length-adjusting element can be provided along the length. When goggles are worn with a helmet, provisions can be made for the strap to pass over the helmet. The clip portions can be extended outwardly such that the width of the helmet does not cause the strap to pull the goggle frame away from the smaller contour of the user's face.

If goggles with outwardly extended clips are worn without a helmet, the strap does not function effectively with the outwardly extended clip portions and can be uncomfortable to wear in that the strap does not conform to the shape of the user's head.

One solution to the aforementioned problem is proposed by U.S. Pat. No. 6,928,663 or 6,732,383 wherein the clip portions are hinged to the goggle frame to pivot outwardly when the goggles are worn with a helmet or inwardly when worn without a helmet.

Goggles are known which incorporate electrical or signal systems. Goggles having electrical, controllable, variable light color density lenses are known, such as disclosed in U.S. Pat. No. 5,172,256. Goggles having electrical ventilation are known, such as disclosed in U.S. Pat. No. 4,150,443. Goggles having a lens electrical heating element are known, such as disclosed in U.S. Pat. No. 4,942,629 or 4,868,929. Goggles having a signal system for aiming a hand held weapon are known, such as disclosed in U.S. Pat. No. 5,379,140. For these electrical or signal conducting systems, provisions are made to deliver electrical power or signals to the frame through electrical conductors.

The present inventors have recognized that it would be desirable to provide clip portions for goggle frames that allowed the goggle frame to be worn effectively with a helmet or without a helmet. The present inventors have recognized that it would be desirable to provide a goggle frame with clip portions that more effectively accommodated electrical or signal systems.

The present inventors have recognized that it would be desirable to provide an improved goggle assembly including an electrically controllable system.

SUMMARY OF THE INVENTION

The present invention provides goggles that include reversible clip portions that can accommodate the goggles being worn with or without a helmet, while ensuring an effective fit of the goggles to the user's face.

The present invention provides goggles that include clip portions that can accommodate contacts to conduct electrical power or signals to the goggle frame or lens.

The present invention provides goggles that include clip portions that can accommodate electrical contacts to conduct electrical power or signals to the goggle frame or lens and which are reversible to accommodate the goggles being worn either with or without a helmet, while ensuring a precise and effective fit of the goggles to the user's face and correct electrical or signal conduction to the goggle frame or lens.

The present invention provides goggles that include clip portions that are snap connected to the goggle frame and easily changed in orientation to convert from a helmet configuration to a no-helmet configuration.

The present invention provides goggles that include clip portions that accommodate both a helmet configuration and a no-helmet configuration while maintaining a rigid clip configuration, avoiding the use of hinges which may reduce the structural reliability of the goggles.

The present invention provides goggles that include clip portions that allow for the passing of electrical current or signals from a current-conducting or signal-conducting band to the goggle frame or lens.

According to an exemplary embodiment of the invention, goggles include a strap, a frame, at least one lens, and first and second connectors. The strap has a length and opposite strap free ends. The lens is carried by the frame in front of a user's eyes. The frame has a lateral center and opposite lateral end portions. Each connector has a base portion for connecting to the opposite lateral end portion of the frame, and a strap-mounting portion for connecting to the opposite strap free end of the strap. Each strap-mounting portion has a strap connecting end where the strap meets the strap-mounting portion. Each of the first and second connectors has a first orientation and a second orientation.

The strap connecting end of each connector is located a first lateral distance from the lateral center of the frame when the connector is in a first orientation, and the strap connecting end is located a second lateral distance from the lateral center of the frame when the connector is in a second orientation; the second distance is greater than the first distance.

According to another aspect of the exemplary embodiment, each of the connectors is movable between the first orientation and the second orientation.

According to one aspect of the embodiment of the invention, the first and second connectors are releasably attachable to the frame at the opposite lateral end portions. Each first and second connectors are releasably attachable in the first orientation to a respective lateral end portion of the frame and also releasably attachable to the respective lateral end portion in the second orientation rotated from the first orientation.

According to another aspect of an embodiment of the invention, the base portions of the first and second connectors are releasably rigidly attachable to the frame at the opposite lateral end portions. Each base portion is releasably rigidly attachable in a first orientation to a respective lateral end portion and also releasably rigidly attachable to the respective lateral end portion in a second orientation rotated from the first orientation. The base portion and the strap-mounting portion of each of the first and second connectors connect together at an oblique angle wherein the strap-mounting portion is selectively angled rearward when the respective base portion is rigidly attached in the first orientation and the strap-mounting portion is selectively angled outward when the respective base portion is rigidly attached in the second orientation.

According to another aspect of the embodiment of the invention, the goggles have an electrical system carried by the frame and strap. At least one of the first and second connectors comprises a plurality of first contacts and the frame comprises a plurality of corresponding second contacts. The first and second contacts are arranged to touch to effectively connect the electrical system when the base portion is connected to the respective lateral end portion in either the first orientation or the second orientation.

According to another aspect of the embodiment of the invention, the electrical system has a power source holder carried by the strap, and plurality of electrical conductors carried by the strap. The holder is connectable to the electrical conductors on either face of the strap. The power source holder can be a battery holder. The battery holder has contacts connectable to a battery held thereby. The contacts are electrically connected to the conductors. The holder is carried by the strap via a connector mounted on the strap and electrically connected to the conductors. The holder and connector have corresponding releasable contacts such that the holder can be selectively mounted on either face of the strap to make effective electrical connection with the connector.

According to another aspect of the embodiment of the invention, the electrical system powers one member of the following group consisting of: a ventilation fan, a variable light color density lens, a heated lens, and a weapon aiming device. Any member of the group may be carried on the goggles.

According to another aspect of the embodiment of the invention, each of the first and second connectors comprise an engagement bar, and the frame comprises a latch for releasably retaining the engagement bar to the lateral end portion. The engagement bar has upper and lower mounting tabs, and each lateral end portion of the frame comprises receptacles for receiving the mounting tabs.

According to another aspect of the embodiment of the invention, the electrical system is carried by the frame and strap. The electrical system includes a power source carried by the strap electrically connected to two electrical conductors carried by said strap conducting a positive and negative polarity respectively. The first connector comprises a first contact and a second contact, the first connector connected to either the negative polarity or the positive polarity, the second connector connected to the polarity opposite of the polarity connected to the first connector. The frame comprises three corresponding contacts, a middle one of the three corresponding contacts making contact with the first contact in both the first orientation and the second orientation of the first connector, and one of the remaining three corresponding contacts making contact with the second contact depending on whether the connector is in the first orientation or the second orientation.

Numerous other advantages and features of the present invention will be become readily apparent from the following detailed description of the invention and the embodiments thereof, the claims and from the accompanying drawings.

DESCRIPTION OF THE PREFERRED EMBODIMENTS

While this invention is susceptible of embodiment in many different forms, there are shown in the drawings, and will be described herein in detail, specific embodiments thereof with the understanding that the present disclosure is to be considered as an exemplification of the principles of the invention and is not intended to limit the invention to the specific embodiments illustrated.

FIGS. 1-4 illustrate goggles 20 of the present invention. The goggles 20 include a frame 24, at least one lens 26 carried by the frame 24, clip or connector portions 28, 30, and a strap assembly 36. The strap assembly 36 includes a strap 38, a length adjustment buckle 42, and a battery pack 46. The strap 38 includes free end portions 38a, 38b that are connected to the clip portions 28, 30.

Figure 1:
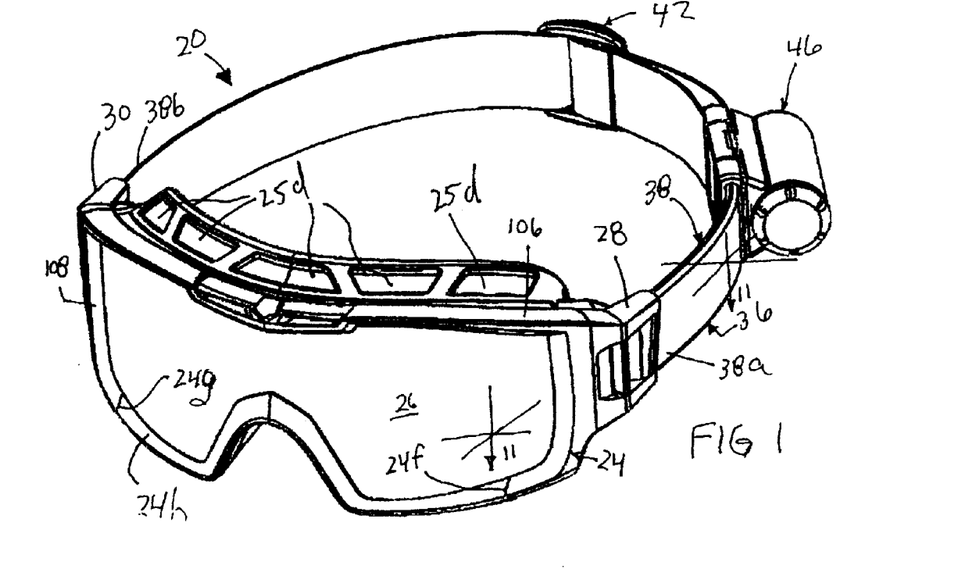
FIG. 1 is a front, top perspective view of goggles according to the present invention.
Figure 1A:
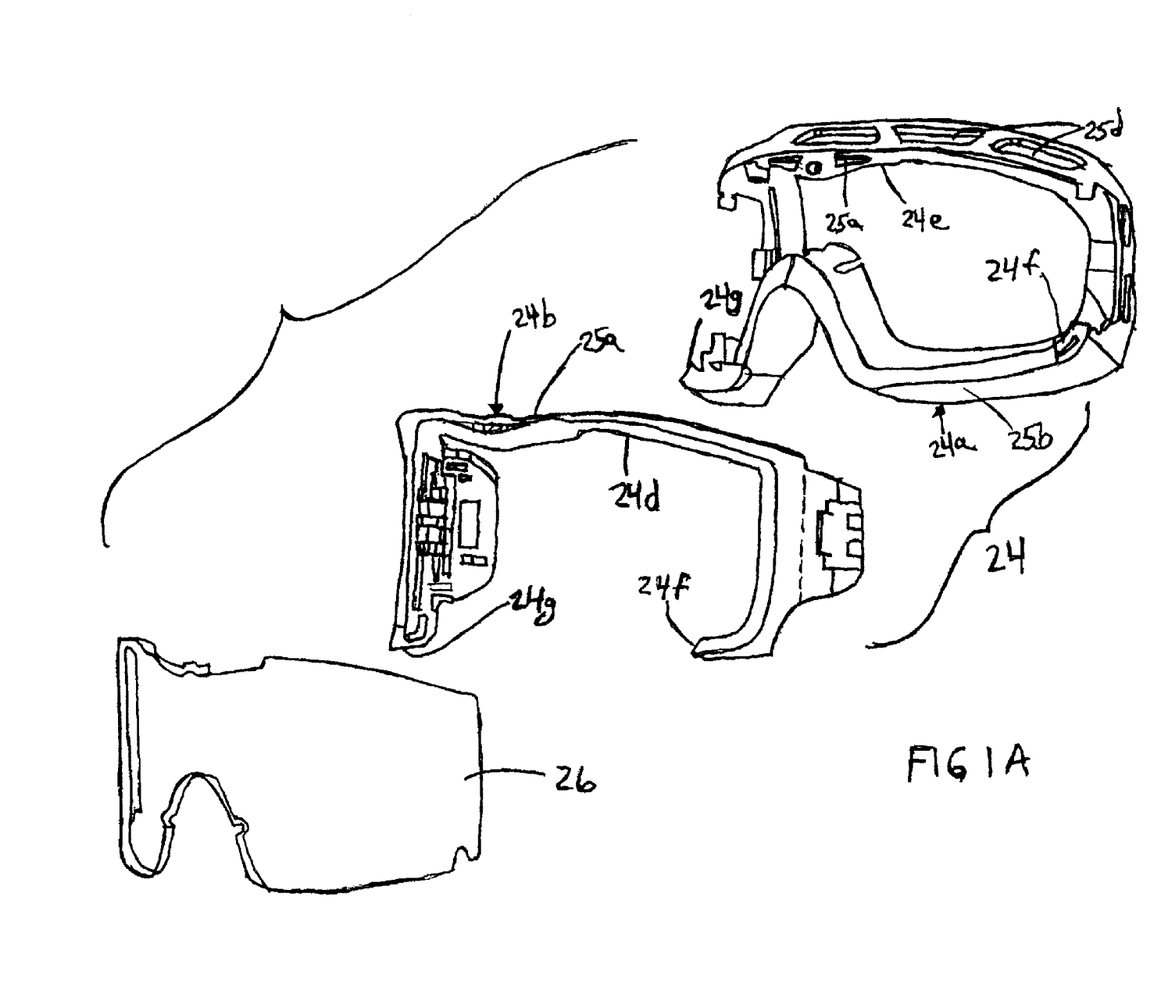
FIG. 1A is an exploded perspective view of a portion of the goggles shown in FIG. 1.

FIG. 1A illustrates the frame 24 comprises a soft frame portion or gasket 24a that closely conforms the goggles against the wearer's face. The frame 24 also includes a hard frame portion 24b. An upper air vent 25a extends through an upper brow part 24d of the hard frame portion 24b and an upper brow part 24e of the gasket 24a and delivers air into or out of the interior region defined between the goggles and the wearer's face. The soft frame portion 24a includes left and right ducted vents 25b that direct air through the soft frame portion 24a into or out of the interior region. The soft frame portion 24a also includes left and right bottom vents 25c (see FIG. 2) that direct air through the soft frame portion 24a into or out of the interior region. The gasket 24 also includes upper vents 25d that also allow air to permeate into or out of the interior area. The vents 25a-25d can be covered by filter material, such as porous foam.

The hard frame portion 24b is fixed to the soft frame portion 24a by a tongue and groove arrangement across the brow parts 24d, 24e of the respective hard frame portion 24b and the soft frame portion 24a, and side plugs and slots between the hard frame portion 24b and the soft frame portion 24a. These connections can be fixed using adhesive.

The hard frame portion 24b does not surround the lens 26 but only extends to interfaces 24f, 24g (FIG. 1) where the hard frame portion 24b smoothly transitions to a lower rim portion 24h of the soft frame portion 24a.

The gasket 24a is preferably composed of a soft, flexible material, such as polyurethane and the hard frame portion 24b and the clips 28, 30 are preferably composed of a hard material such as nylon, such as available from DuPont as ZYTEL ST801.

FIGS. 2A-2D illustrate the strap assembly 36 in more detail. The adjustment buckle 42 is of a conventional design and is used to adjust the effective length of the strap 38 for proper fit to the user's head or helmet worn by the user. The battery pack 46 includes a battery holder 62 that carries a battery 64, and a strap mounted connector 68. The holder 62 includes spring-loaded contacts: a positive contact 74 and a negative contact 76. The contacts 74, 76 are wired internal of the holder 62 (not shown) to be electrically connected to the positive and negative terminals of the battery 64. The holder 62 includes a clasp portion 80 that is hinged to a base portion 83 that when closed together define a slot 82 that receives the connector 68. When the clasp portion 80 is rotated downward onto the base portion 83 in the direction marked "A" the connector 68 is captured in the slot 82. A latch 84 is provided on the base portion 83 that engages the clasp portion 80 to securely engage the holder 62 to the connector 68.

As an alternative, the battery 64 and the holder 62 can be formed as an integral or unitary part that is replaced as a unit.

Figure 2:
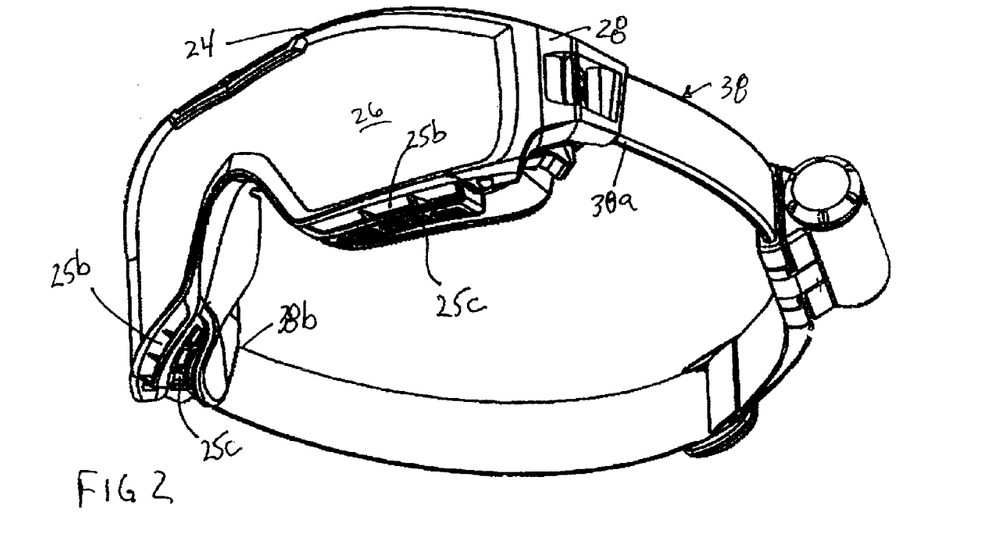
FIG. 2 is a front, bottom perspective view of the goggles of FIG. 1.
Figures 2A, 2B:
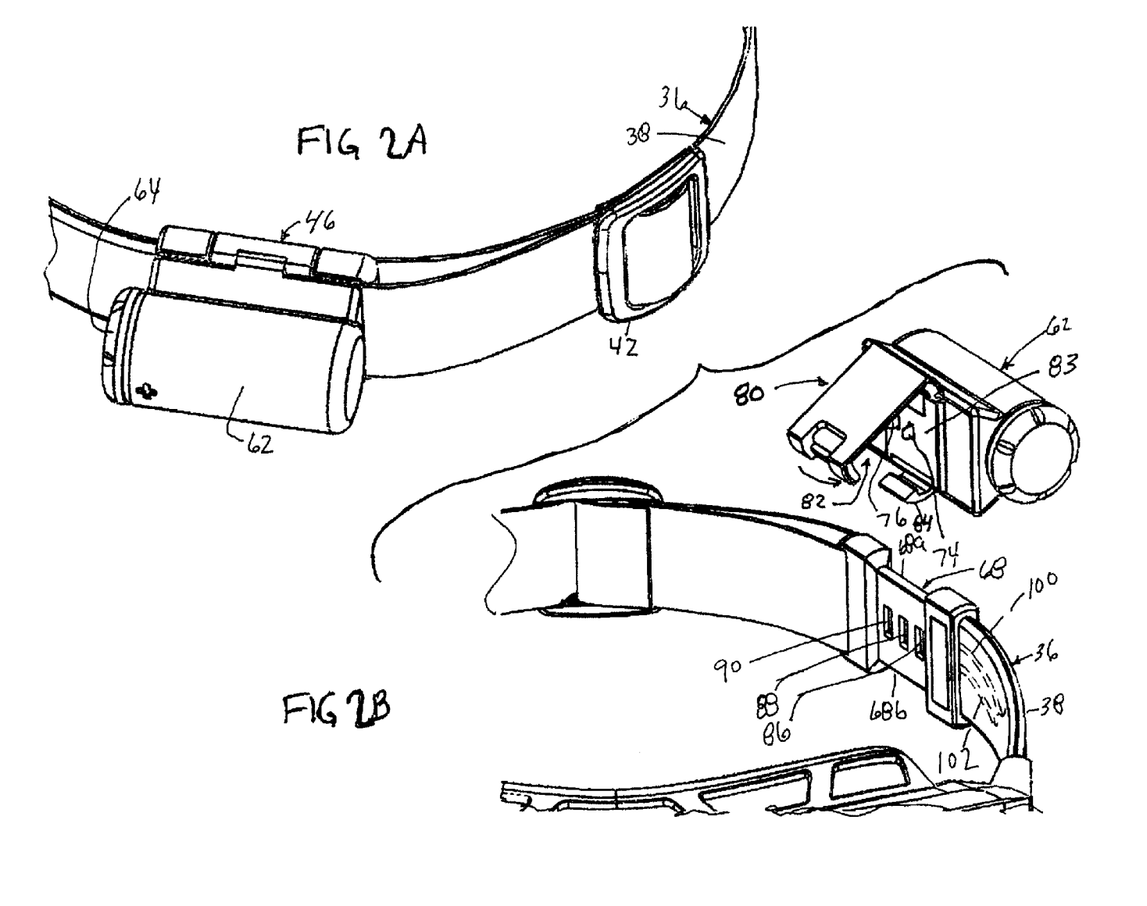
FIG. 2A is a fragmentary perspective top rear view of a portion of the goggles shown in FIG. 1.
FIG. 2B is an exploded fragmentary perspective top rear view of the portion of the goggles shown in FIG. 2A.

The connector 68 includes contact pads 86, 88, 90, two pads of which are arranged to be in electrical contact with the contacts 74, 76. The middle contact pad 88 is electrically connected to a conductor 100, and can be electrically connectable to the negative battery contact 76, and the outer contact pads 86, 90 are electrically connected to a conductor 102, and can be electrically connectable to the positive battery contact 74. The conductors 100, 102 extend from the battery pack 46 to the clip portion 28. The conductors 100, 102 can be wires, threads, or other conducting means that are adhered to, woven into, overlaid onto, or otherwise carried by the strap 38.

Figures 2C, 2D:
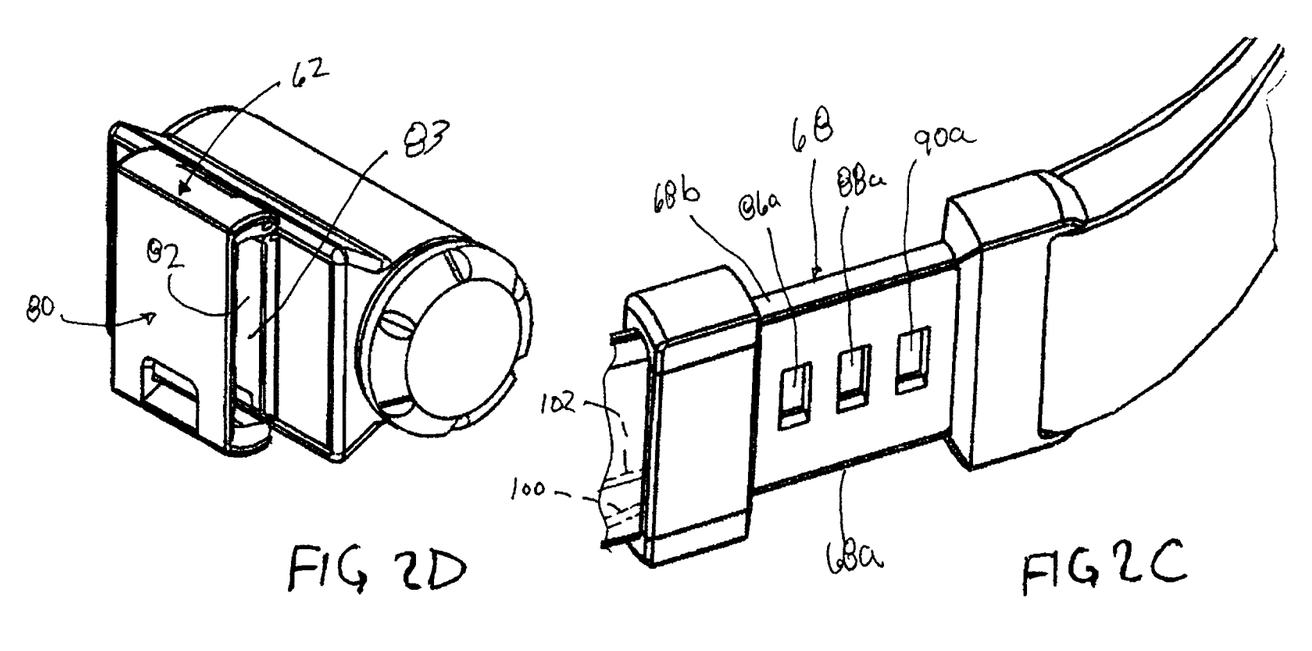
FIG. 2C is an exploded fragmentary perspective view of a portion of the goggles shown in FIG. 2B, turned over.
FIG. 2D is a front, top perspective view of a portion of the goggles shown in FIG. 2B.

FIG. 2B illustrates the connector 68 oriented having a first edge 68a on top and a second edge 68b on bottom. FIG. 2C illustrates a reverse side of the connector 68 after the strap 38 is turned over per the arrow 1C in FIG. 2B, wherein the first edge 68a is now oriented on the bottom and the second edge 68b is now oriented on the top. The connector 68 includes opposite side contact pads 86a, 88a, 90a. The middle contact pad is electrically connected to the conductor 100 and the outer contact pads 88a, 90a are electrically connected to the conductor 102.

FIG. 2D shows a front side of the holder 62 with the clasp portion 80 engaged to the base portion 83 (without the connector 68).

Referring to FIGS. 1, 2, 3 and 4, the clips 28, 30 are releasably rigidly connected to lateral end portions 106, 108 of the frame 24. The clips 28, 30 are mirror image identical so only the clip 28 will be described. The clip 28 includes a base portion 110 and a strap-mounting portion 114. The base portion 110 has a front contour 110a that is substantially flushly continuous with a front contour 106a of the lateral end portion 106. The base portion 110 is formed rigidly with the strap-mounting portion 114. The strap-mounting portion has a front contour 114a that is obliquely angled from the front contour 110a. The oblique angling of the front contour 114a directs the strap-mounting portion 114 rearward toward the user's ear. The oblique angling allows for the strap 38 to closely encircle the user's head to provide a comfortable, aesthetically pleasing, aerodynamic fitment of the goggles to a user not wearing a helmet under the goggle strap 38.

FIGS. 5-8 illustrate the goggles 20 being worn with a helmet 126. In order to allow the strap 38 to pass over and around the helmet 126, the clips 28, 30 oriented per FIG. 1 are removed from the frame 24 and turned 180 degrees from the orientation shown in FIG. 1, and re-installed. A surface contour 110b that is opposite to the surface contour 110a is now substantially flushly continuous with the surface contour 106a. A surface contour 114b that is opposite to the surface contour 114a is arranged at an oblique angle to the surface contour 110b. The strap-mounting portion 114 is now obliquely angled to extend in a direction substantially outward, away from a side of the user's head. By extending outward, the strap 38 connected to the strap-mounting portion 114 can more easily surround an outside perimeter of the helmet 126 without pulling the lateral end portion 106 away from the user's face. A comfortable and effective sealing or fit onto the user's face is achieved.

Figure 3:
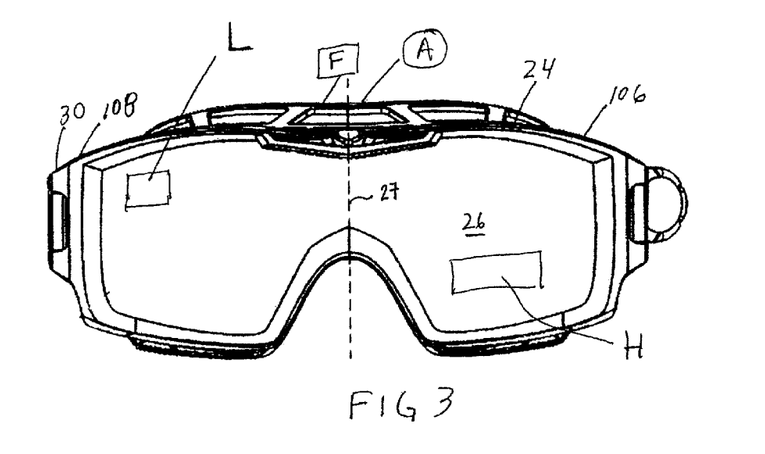
FIG. 3 is a front view of the goggles of FIG. 1.
Figure 4:
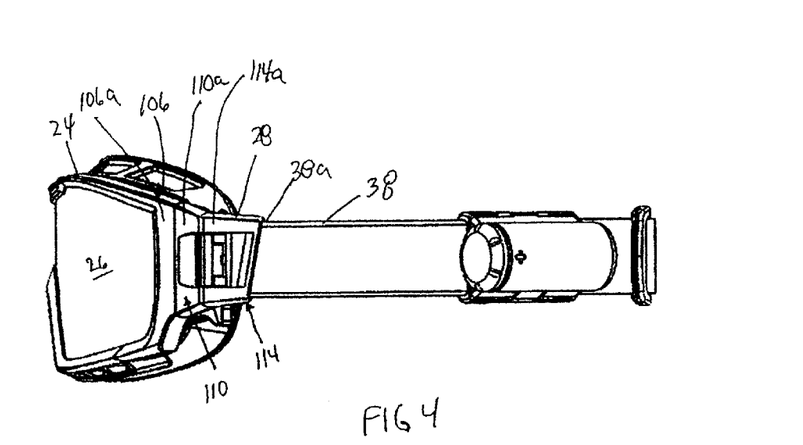
FIG. 4 is a side view of the goggles of FIG. 1.
Figures 5, 6:
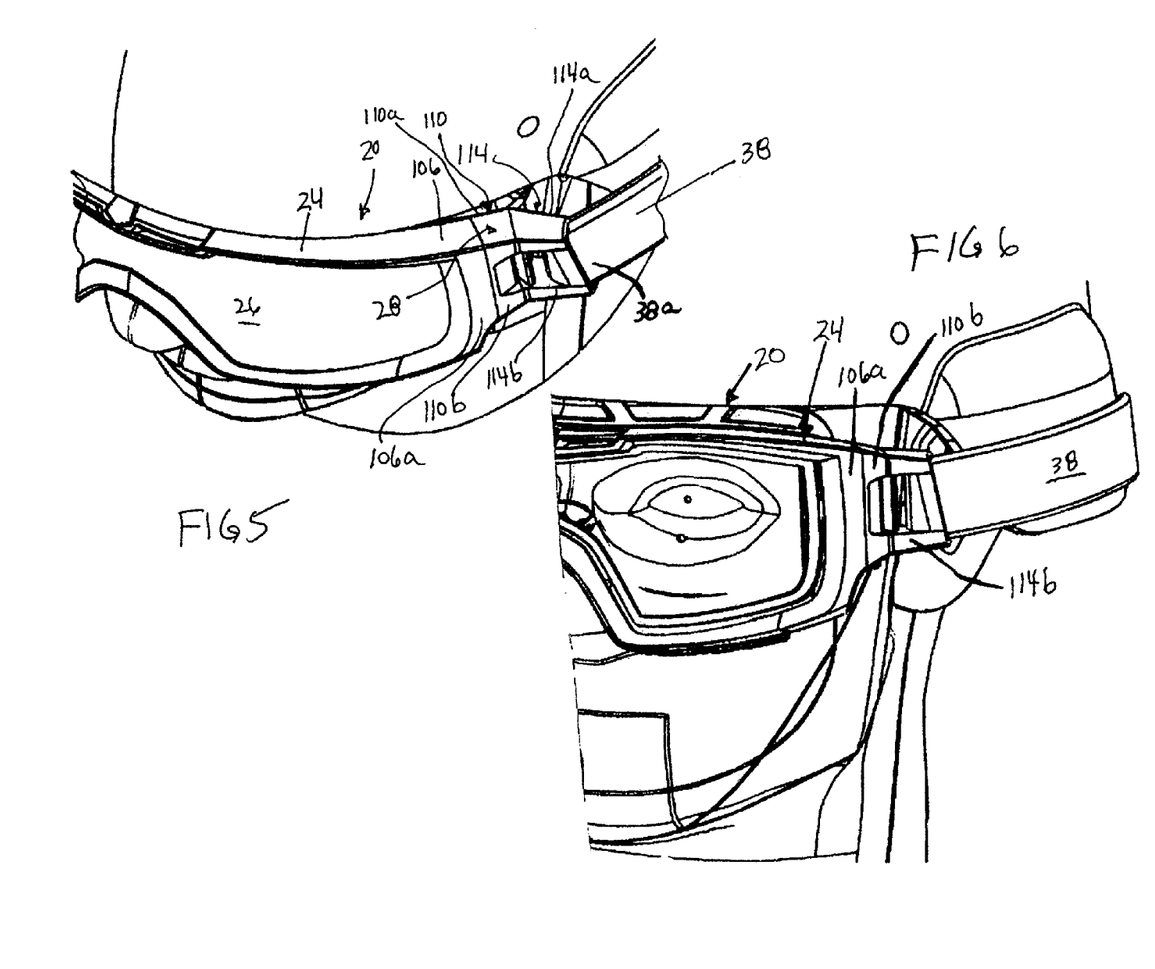
FIG. 5 is a fragmentary top front perspective view of the goggles of FIG. 1 having clip portions reversed for using the goggles with a helmet.
FIG. 6 is a fragmentary side perspective view of the goggles shown in FIG. 5.
Figure 7:
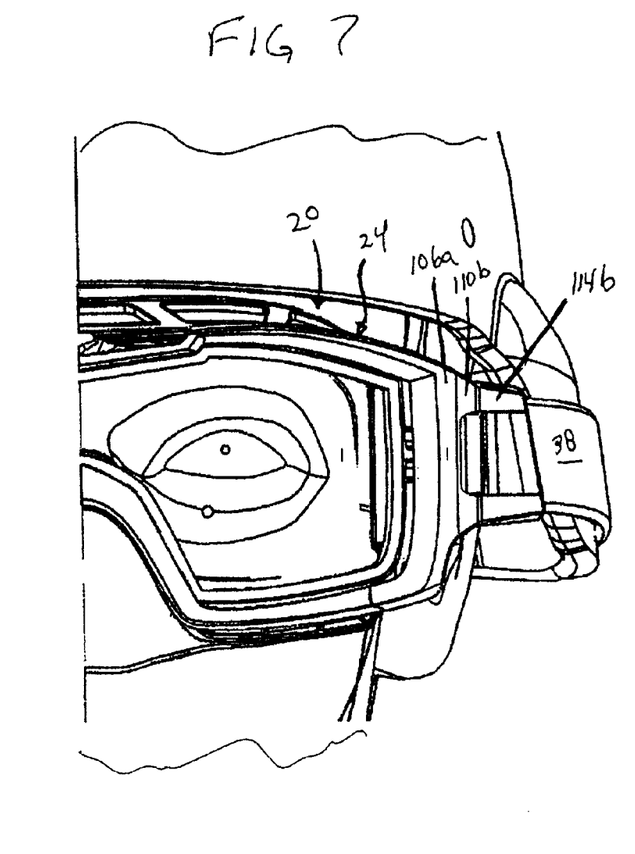
FIG. 7 is a fragmentary front view of the goggles of FIG. 5.
Figure 8:
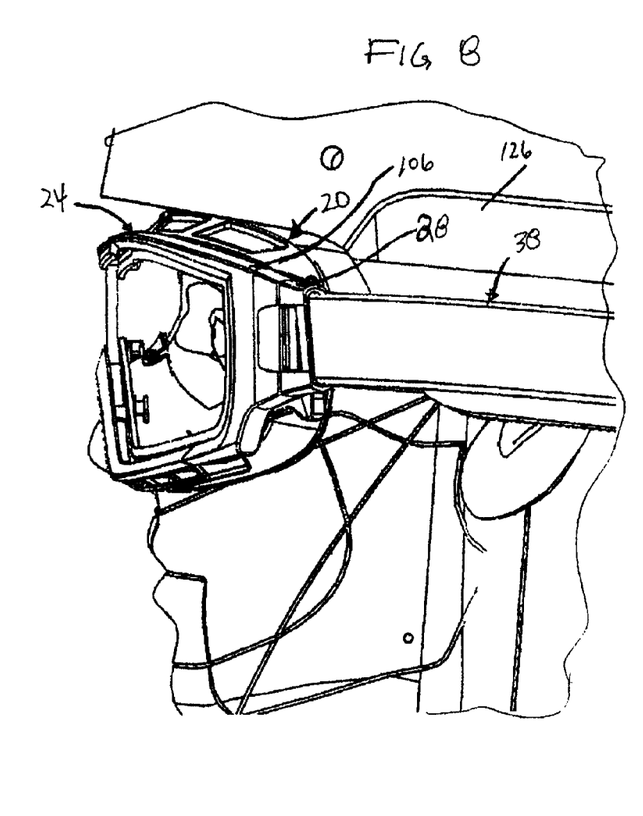
FIG. 8 is a side view of the goggles of FIG. 5.

The frame 24 has a lateral center 27 as shown in FIG. 3. A strap connecting end 114c (FIG. 4) of the strap mounting portion 114 of the clips 28, 30 has a first lateral distance from the lateral center 27 of the frame when the clips 28, 30 are orientated as shown in FIGS. 1, 2, 3, and 4. The strap connecting end 114c (FIG. 4) of the strap mounting portion 114 of the clips 28, 30 has a second lateral distance from the lateral center 27 of the frame when the clips 28, 30 are orientated as shown in FIGS. 5, 6, 7, and 8. The second lateral distance is greater than the first lateral distance. Therefore, when the clips 28, 30 are orientated as shown in FIGS. 5 and 6, the strap connecting end 114c (FIG. 5) of the strap mounting portion 114 of the clips 28, 30 is a lateral distance farther from the lateral center 27 of the frame than when the clips are orientated as shown in FIGS. 1, 2, 3, and 4.

Figures 9, 10:
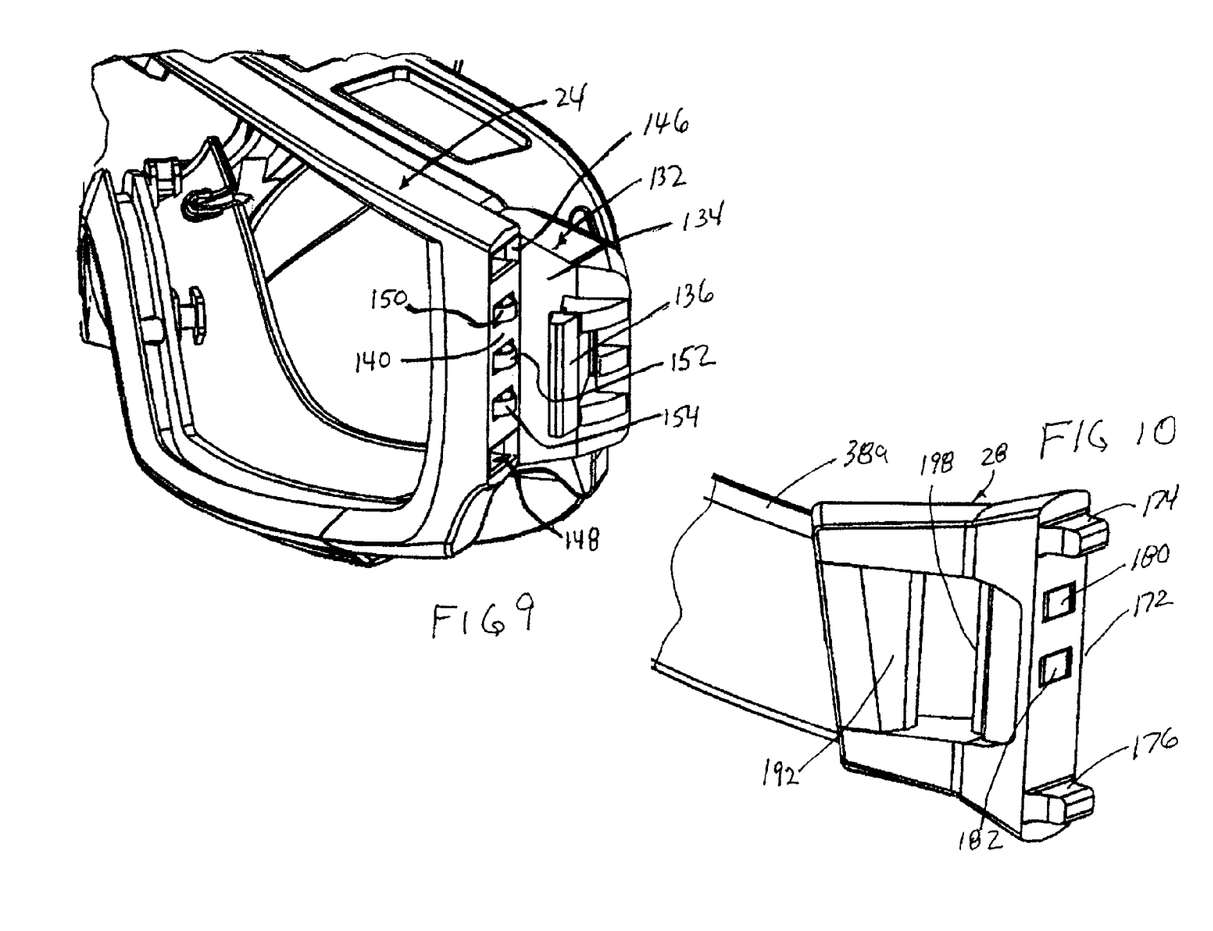
FIG. 9 is fragmentary top front perspective view of a frame portion of the goggles of FIG. 1.
FIG. 10 is a fragmentary side perspective view of a clip portion of the goggles of FIG. 1.

FIG. 9 illustrates the lateral end portion 106 of the frame 24. Additionally, the frame 24 includes an attachment housing 132 that includes a backing plate 134 and a latch 136 extending therefrom. The frame 24 can be a unitary part including the lateral end portions 106, 108, and the attachment housing 132. The lateral end portion 106 includes an engagement surface 140. The base portion 110 of the clip 28 mates with the surface 140 once the clip 28 is installed. The surface 140 includes two rectangular sockets 146, 148 and three spring-loaded electrical contact pads 150, 152, 154. An electronic device, such as a circuit board 160 having circuit elements 162, 164, 166 is shown in FIGS. 11-14. The contact pads 150, 152, 154 are electrically connected to conductors within the circuit board 160 and interact with the circuit elements 162, 164, 166.

The particular electronic device that is electrically connected through the clip 28 of the present invention is not limited as to function and, for example, can be used to control variable light color density lenses L (FIG. 3) such as disclosed in U.S. Pat. Nos. 4,968,127 and 5,172,256; to ventilate goggles by fan F (FIG. 3), such as disclosed in U.S. Pat. No. 4,150,443; to heat lenses by element H (FIG. 3), such as disclosed in U.S. Pat. No. 4,942,629 or 4,868,929; or to assist in aiming a hand held weapon by device A (FIG. 3), such as disclosed in U.S. Pat. No. 5,379,140, all patents herein incorporated by reference. Elements L, F, H and A are all shown schematically in FIG. 3.

FIG. 10 illustrates the clip 28 including an engagement bar 172 having protruding tabs 174, 176 and electrical contacts 180, 182. The strap end portion 38a is adhesively secured within a slot 190 formed within a strap-mounting bar 192, shown in FIG. 11. The conductor 102 is electrically connected to the contact 182 via a conducting element 102a embedded within the material of the clip. The conductor 100 is electrically connected to the contact 180 via a conductor element embedded within the material of the clip (not shown).

As can be understood from FIGS. 9 and 10, the electrical contact 180 will either make electrical contact with the spring-loaded contact pad 150 or the spring-loaded contact pad 154 depending on the selected orientation of the clip with respect to the end portion 106. The electrical contact 182, being centered on the engagement surface 140 will make electrical contact with the middle spring-loaded contact pad 152 in either orientation of the clip 28.

Figure 11:
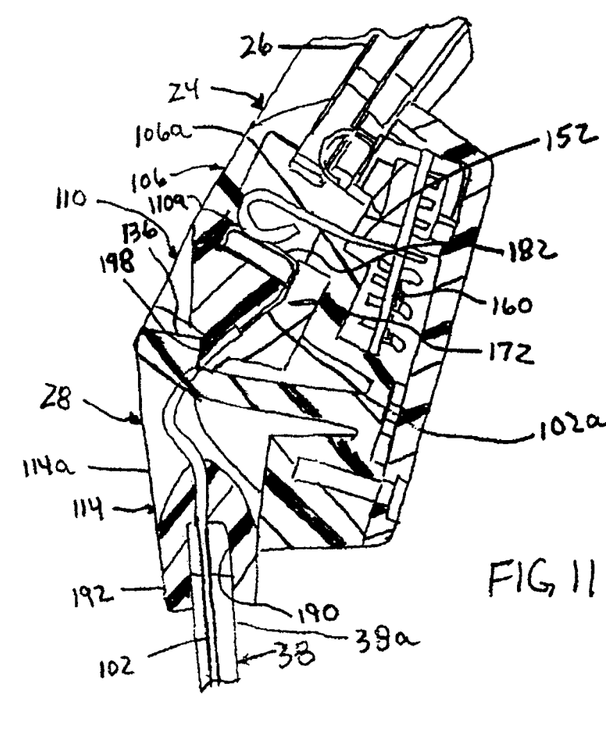
FIG. 11 is a fragmentary sectional view taken generally along line 11-11 of FIG. 1.
Figure 12:
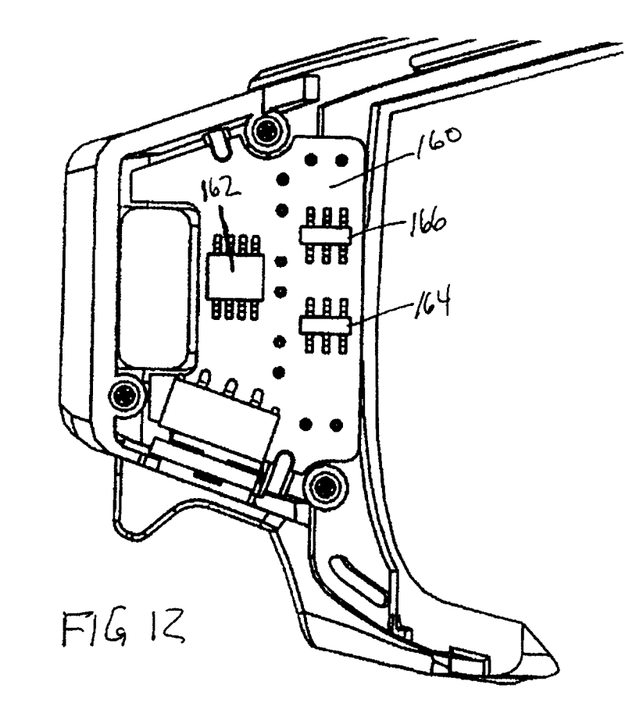
FIG. 12 is a fragmentary rear view of a portion of the goggles of FIG. 1 with a rear cover removed.
Figure 13:
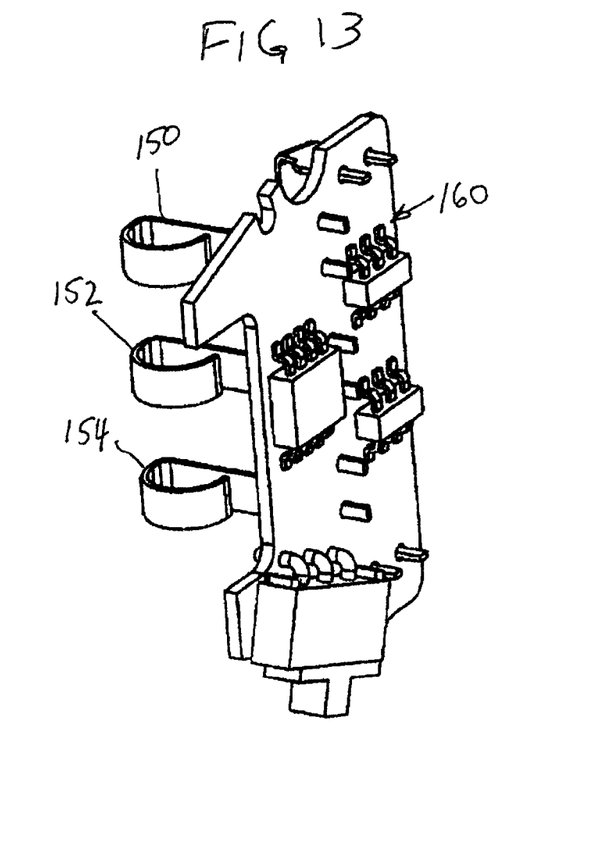
FIG. 13 is a rear perspective view of an electronic card taken from FIG. 12.
Figure 14:
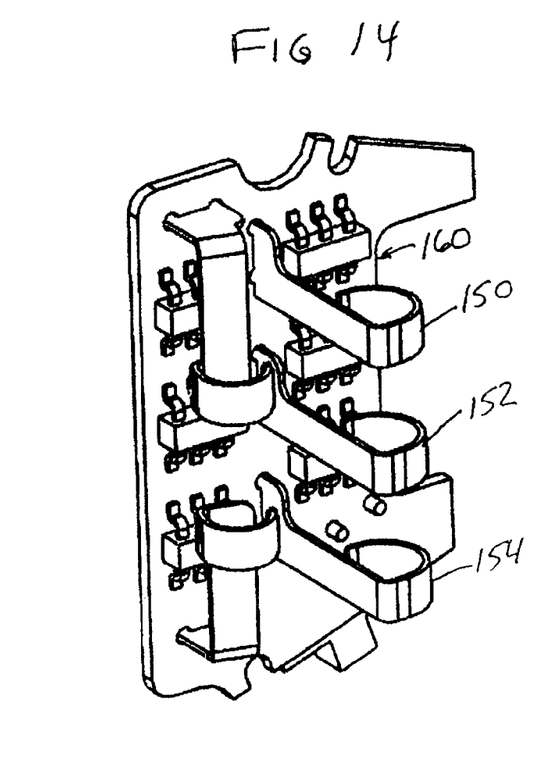
FIG. 14 is a front perspective view of the electronic card of FIG. 13.

FIG. 11 shows the clip 28 installed to the end portion 106 using the orientation shown in FIGS. 1-4. The latch 136 has engaged a tip portion 198 of the engagement bar 172. The protruding tabs 174, 176 are pressed tightly into the sockets 146, 148. The contacts 152, 182 are pressed together, as are the contacts 150, 180 (not shown). The oblique angle between the base portion 110 and the strap-mounting portion 114 allows the strap 38 to extend rearward in a direction toward the user's ear. A cover plate 206 is attached to a backside of the attachment housing 132 by screws to enclose the circuit board 160.

Figure 15A:
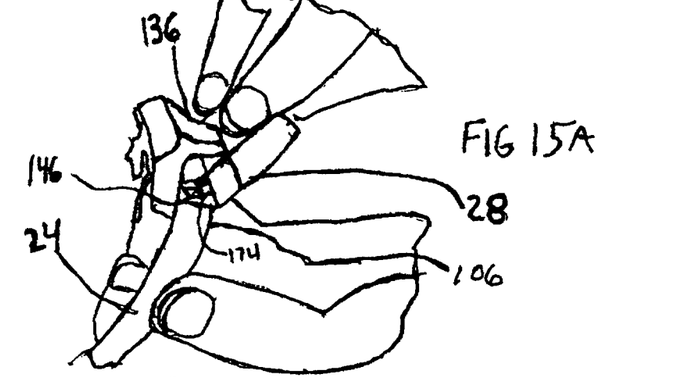
FIG. 15A-15C are fragmentary top perspective views demonstrating the installation of the clip portion to the frame portion in progressive steps.
Figure 15B:
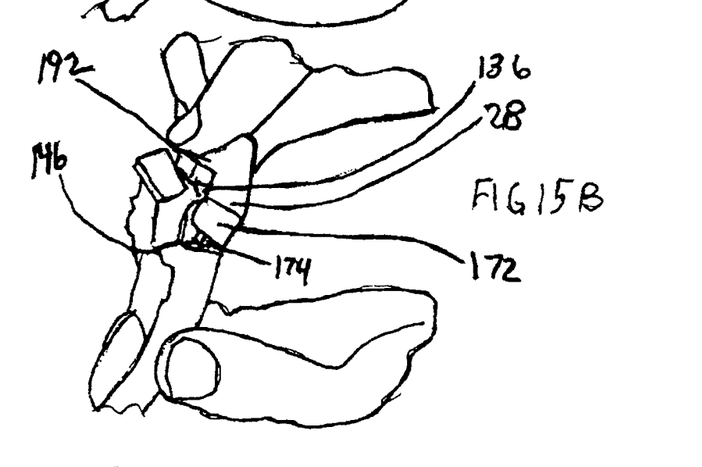
Figure 15C:
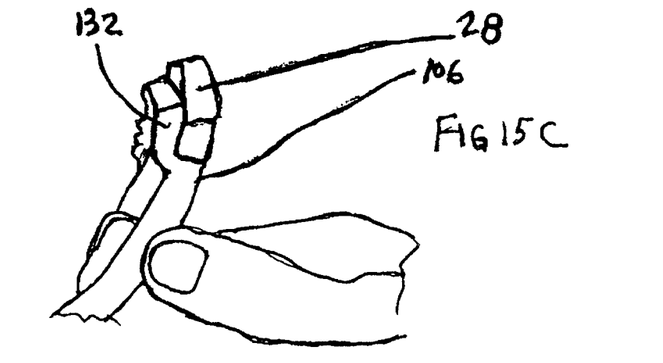

FIGS. 15A-15C illustrate the snap engagement of the clip 28 to the end portion 106 of the frame 24. The clip 28 is pushed at an angle beneath the latch 136, and the tabs 174, 176 are pushed into the sockets 146, 148. The latch 136 passes through the space between the engagement bar 172 and the strap-mounting bar 192 as the tabs 174, 176 are pushed into the sockets 146, 148. When the clip 28 is fully engaged, the tabs 174, 176 are fully seated into the sockets 146, 148, the contacts 180, 182 are electrically contacted with the spring-loaded contact pads 150, 152, and the latch 136 snaps over the rear edge of the engagement bar 172, preventing inadvertent disengagement of the clip 28 from the frame 24.

To install the clip 28 in the orientation shown in FIGS. 5-8, the latch 136 is lifted with a finger away from the tip portion 198 and the clip 28 is pivoted away from the attachment housing 132 according to a reverse progression of FIGS. 15C to 15A. The clip 28 is then turned approximately 180 degrees and installed in substantially the same fashion as shown in FIGS. 15A to 15C. Since both clips 28, 30 are turned over, the strap 38 must also be turned over. In order for the battery 64 to be located outside of the strap 38, to prevent interference between the battery and the back of the user's head or helmet, the holder 62 must be reversed and reinstalled onto the attachment 68, with the battery 64 located on a rear side of the strap 38.

The connector 68 includes the three contact pads 86, 88, 90 and the three contact pads 86a, 88a, 90a on each respective side thereof to allow for the holder 62 and the contacts 74, 76 therein to be in electrical connection with the correct conductor. The contact 76 (negative) will contact either of the contact pads 88 or 88a and the contact 74 (positive) will contact one of the contact pads 86, 90, 86a, 90a. The pads 88, 88a are electrically connected to the conductor 102 and the pads 86, 90, 86a, 90a are electrically connected to the conductor 100. Thus, the contact 74 will be electrically connected to the positive conductor 102 and the contact 76 will be electrically connected to the negative conductor 100 no matter the orientation of the holder on either side of the strap 38.

Although clip 30 is essentially identical to the described clip 28, if electrical connection through the clip 30 is not needed, the electrical conducting features can be eliminated from clip 30.

Figure 16:
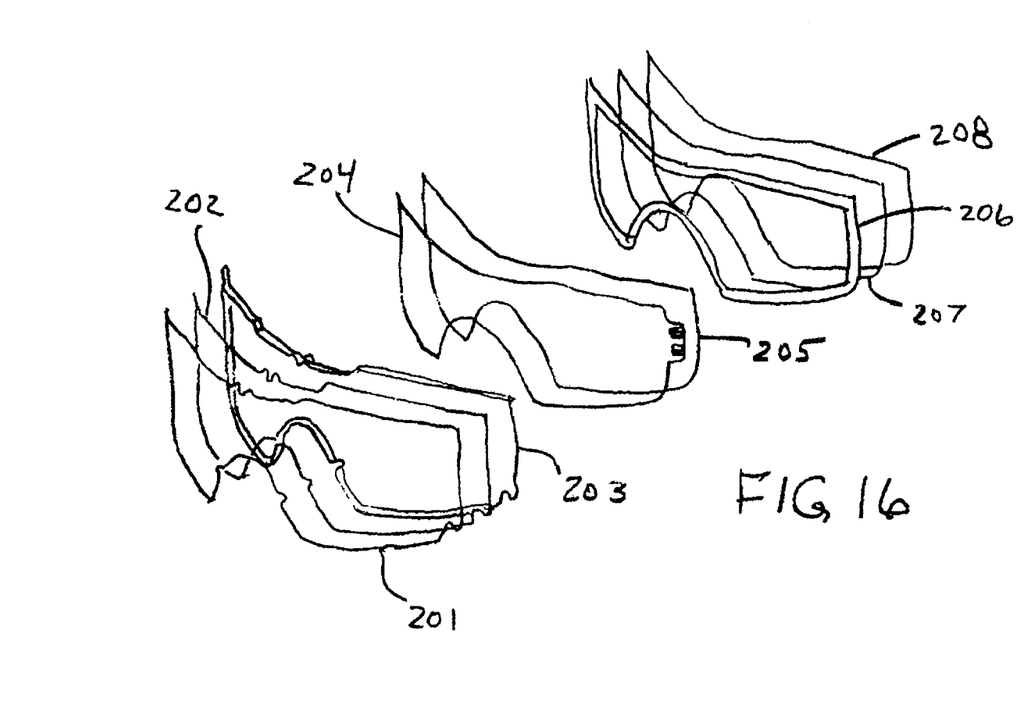
FIG. 16 is an exploded perspective view of a lens assembly taken from FIG. 1.

FIG. 16 illustrates a preferred construction of the lens 26 according to another aspect of the invention. The lens 26 is formed as a laminate with the following layers:
  anti-reflective coating 201,
  hard coating 202,
  polycarbonate lens 203,
  variable light transmission lens 204,
  anti-reflective coating 205,
  foam gasket providing 1.6 mm air gap 206,
  anti-reflective coating 207, and
  anti-fog film 208.

From the foregoing, it will be observed that numerous variations and modifications may be effected without departing from the spirit and scope of the invention. It is to be understood that no limitation with respect to the specific apparatus illustrated herein is intended or should be inferred.

The invention claimed is:

1. Goggles comprising:
  a strap having a length and opposite strap free ends;
  a frame having a lateral center and opposite lateral end portions;
  at least one lens carried by said frame in front of a user's eye; and
  a first connector and a second connector each having a base portion for connecting to one of said opposite lateral end portions of said frame, and a strap-mounting portion for connecting to said opposite strap free end of said strap;
  each strap-mounting portion has a strap connecting end where said strap meets said strap-mounting portion;
  each of said first and second connectors has a first orientation and a second orientation;
  wherein the strap connecting end of each connector is located at a first lateral distance from said lateral center of said frame when said connector is in the first orientation and the respective base portion is connected to the frame, and the strap connecting end is located at a second lateral distance from said lateral center of said frame when said connector is in the second orientation and the respective base portion is connected to the frame; the second distance being greater than the first distance; and
  further comprising an electrical system carried by said frame and strap, wherein at least one of said first and second connectors comprises a plurality of first electrical contacts and said frame comprises a plurality of corresponding second electrical contacts, said first and second electrical contacts arranged to form an electrical connection when said base portion is connected to the respective lateral end portion in either the first orientation or the second orientation.

2. The goggles according to claim 1, wherein said electrical system comprises a power source holder carried by said strap, and a plurality of electrical conductors carried by said strap, said holder is connectable to said electrical conductors on either face of said strap.

3. The goggles according to claim 2, wherein the power source holder is a battery holder.

4. The goggles according to claim 1, wherein said electrical system comprises a power source carried by said strap and having contacts connectable to a power source held thereby and connected to said conductors; wherein said holder comprises a first portion mounted on said strap and connected to said conductors and a second portion holding said power source, said first portion and said second portion having corresponding releasable contacts such that said second portion can be selectively mounted on either face of said strap to make effective electrical connection with said first portion.

5. The goggles according to claim 1, wherein the electrical system powers one member of the following group consisting of: a ventilation fan, a variable light color density lens, a heated lens, and a weapon aiming device; said member of said group being carried on said goggles.

6. Goggles comprising:
a strap having a length and opposite strap free ends;
at least one lens adapted to be positioned in an upright orientation where the lens is positioned in front of a user's eyes with the user's head held upright;
a frame having a lateral center and opposite lateral end portions, said at least one lens carried by said frame in front of a user's eye;
a first connector and a second connector each having a base portion for releasably connecting to one of said opposite lateral end portions of said frame, and a corresponding strap-mounting portion for connecting to said opposite strap free end of said strap;
each strap-mounting portion has a strap connecting end where said strap-mounting portion connects to said strap;
each of said first and second connectors is releasably rigidly attached to said frame by respective base portions in a selectable one of a first orientation or a second orientation;
wherein the strap connecting end of each connector is located at a first lateral distance from said lateral center of said frame when said connector is in the first orientation and the respective base portion is connected to the frame, and the strap connecting end is located at a second lateral distance from said lateral center of said frame when said connector is in the second orientation and the respective base portion is connected to the frame, the second distance being greater than the first distance; and
first and second latches that rigidly attach the first and second connectors to the frame, given the lens being oriented in the upright orientation, once the first and second connectors are engaged to the lateral end portions in either the first orientation or the second orientation,
wherein the first and second latches are each mounted to a respective one of the lateral end portions, and said base portions each comprise an engagement bar that is engaged by a respective latch when the first and second connectors are engaged to the lateral end portions in either the first orientation or the second orientation,
and wherein each said engagement bar comprises a tab and the respective lateral end portion comprises a socket for receiving the tab, wherein the base portion is engaged to the lateral end when the tab is inserted into the socket and the engagement bar is pivoted until the engagement bar snaps behind the latch.

7. Goggles comprising:
a strap having a length and opposite strap free ends;
at least one lens adapted to be positioned in an upright orientation where the lens is positioned in front of a user's eyes with the user's head held upright;
a frame having a lateral center and opposite lateral end portions, said at least one lens carried by said frame in front of a user's eye;
a first connector and a second connector each having a base portion for releasably connecting to one of said opposite lateral end portions of said frame, and a corresponding strap-mounting portion for connecting to said opposite strap free end of said strap;
each strap-mounting portion has a strap connecting end where said strap-mounting portion connects to said strap;
each of said first and second connectors connect to said frame by respective base portions in a selectable one of a first orientation or a second orientation;
wherein the strap connecting end of each connector is located at a first lateral distance from said lateral center of said frame when said connector is in the first orientation and the respective base portion is connected to the frame, and the strap connecting end is located at a second lateral distance from said lateral center of said frame when said connector is in the second orientation and the respective base portion is connected to the frame, the second distance being greater than the first distance;
an electrical system carried by said frame and strap, wherein at least one of said first and second connectors comprises a plurality of first contacts and said frame comprises a plurality of corresponding second contacts, said first and second contacts arranged to touch to effectively connect the electrical system when said base portion is connected to the respective lateral end portion in either the first orientation or the second orientation.

8. Goggles comprising:
a strap having a length and opposite strap ends;
a frame having opposite lateral end portions;
at least one lens carried by the frame; and
a first connector and a second connector each having a base portion for connecting to one of the opposite lateral end portions of the frame, and each base portion having a corresponding a strap-mounting portion for connecting to one of the opposite strap ends of the strap;
wherein the first connector connects to the frame in a first orientation and a second orientation, wherein in the first orientation, the strap-mounting portion of the first connector extends in a first direction, and in the second orientation, the strap-mounting portion of the first connector extends in a second direction, the first direction being different from the second direction; and
an electrical system carried by the frame and strap, wherein at least one of the first and second connectors comprises a plurality of first electrical contacts and the frame comprises a plurality of corresponding second electrical contacts, the first and second electrical contacts arranged to form an electrical connection when the base portions are connected to the lateral end portions in either of the first orientation and the second orientation.

* * * * *